US 9,345,627 B2
(12) United States Patent
Sperl et al.

(10) Patent No.: US 9,345,627 B2
(45) Date of Patent: *May 24, 2016

(54) DISPOSABLE ABSORBENT ARTICLE HAVING TAILORED LEG EDGES

(71) Applicant: Kimberly-Clark Worldwide, Inc., Neenah, WI (US)

(72) Inventors: Michael Donald Sperl, Waupaca, WI (US); Seth Michael Newlin, Appleton, WI (US); Michael John Faulks, Neenah, WI (US); Gregory John Jansen, Smyrna, DE (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 214 days.

This patent is subject to a terminal disclaimer.

(21) Appl. No.: 14/182,644

(22) Filed: Feb. 18, 2014

(65) Prior Publication Data

US 2014/0163510 A1 Jun. 12, 2014

Related U.S. Application Data

(62) Division of application No. 12/231,213, filed on Aug. 29, 2008, now Pat. No. 8,690,851.

(51) Int. Cl.
*A61F 13/15* (2006.01)
*A61F 13/49* (2006.01)
*A61F 13/494* (2006.01)

(52) U.S. Cl.
CPC ..... *A61F 13/49017* (2013.01); *A61F 13/15609* (2013.01); *A61F 13/15723* (2013.01); *A61F 13/49015* (2013.01); *A61F 13/49019* (2013.01); *A61F 13/49406* (2013.01); *A61F 2013/49025* (2013.01); *A61F 2013/49028* (2013.01); *A61F 2013/49034* (2013.01);

(Continued)

(58) Field of Classification Search
CPC ............... A61F 13/49019; A61F 13/49406; A61F 2013/49039; A61F 13/49017; A61F 13/49038; A61F 2013/49031; A61F 2013/49028

See application file for complete search history.

(56) References Cited

U.S. PATENT DOCUMENTS 2,895,477 A 7/1959 Bernard
4,081,301 A 3/1978 Buell
(Continued)

FOREIGN PATENT DOCUMENTS

EP 0048011 A1 3/1982
EP 0276970 A2 8/1988
(Continued)

*Primary Examiner* — Susan Su
(74) *Attorney, Agent, or Firm* — Kimberly-Clark Worldwide, Inc.

(57) ABSTRACT

A disposable absorbent article comprises a first crotch elastic member adjacent a first crotch edge and a second crotch elastic member adjacent a second crotch edge, each crotch elastic member extending generally in a longitudinal direction, each crotch elastic member having a front terminal point and a rear terminal point. In one embodiment, at least one of the terminal points of the first crotch elastic member is positioned transversely inward from a remaining portion of the first crotch elastic member, and at least one of the terminal points of the second crotch elastic member is positioned transversely inward from a remaining portion of the second crotch elastic member. In another embodiment, front end portions of the first and second crotch elastic members or rear end portions of the first and second crotch elastic members converge transversely inward toward each other.

9 Claims, 2 Drawing Sheets

(52) U.S. Cl.
CPC ............... *A61F 2013/49036* (2013.01); *A61F 2013/49039* (2013.01); *A61F 2013/49041* (2013.01)

(56) References Cited

U.S. PATENT DOCUMENTS

| | | | |
|---|---|---|---|
| 4,892,528 | A | 1/1990 | Suzuki et al. |
| 4,906,243 | A | 3/1990 | Dravland |
| 5,399,219 | A | 3/1995 | Roessler et al. |
| 5,439,459 | A | 8/1995 | Tanji et al. |
| 5,447,508 | A | 9/1995 | Numano et al. |
| 5,500,075 | A | 3/1996 | Herrmann |
| 5,540,672 | A | 7/1996 | Roessler et al. |
| 5,577,540 | A | 11/1996 | Sageser |
| 5,599,338 | A | 2/1997 | Enloe |
| 5,649,919 | A | 7/1997 | Roessler et al. |
| 5,779,689 | A | 7/1998 | Pfeifer et al. |
| 5,814,036 | A | 9/1998 | Roennberg et al. |
| 6,110,158 | A | 8/2000 | Kielpikowski |
| 6,179,820 | B1 | 1/2001 | Fernfors |
| 6,210,387 | B1 | 4/2001 | Rudberg et al. |
| 6,761,711 | B1 | 7/2004 | Fletcher et al. |
| 7,150,729 | B2 | 12/2006 | Shimada et al. |
| 7,226,438 | B2 | 6/2007 | Soga et al. |
| 7,264,614 | B2 | 9/2007 | Minato |
| 2003/0023224 | A1* | 1/2003 | Ishikawa ............ A61F 13/49019 604/385.24 |
| 2003/0078556 | A1 | 4/2003 | Sasaki et al. |
| 2003/0120246 | A1 | 6/2003 | Franklin et al. |
| 2003/0158534 | A1 | 8/2003 | Niki et al. |
| 2004/0010241 | A1 | 1/2004 | Sanders et al. |
| 2004/0030317 | A1 | 2/2004 | Torigoshi |
| 2004/0092903 | A1 | 5/2004 | Olson et al. |
| 2004/0225270 | A1 | 11/2004 | Hermansson et al. |
| 2005/0004545 | A1 | 1/2005 | Shimada et al. |
| 2005/0261652 | A1 | 11/2005 | Digiacomantonio et al. |
| 2006/0161128 | A1 | 7/2006 | Soga et al. |
| 2006/0200109 | A1 | 9/2006 | Oba et al. |
| 2006/0259003 | A1 | 11/2006 | Venkitaraman et al. |
| 2007/0073262 | A1 | 3/2007 | Babusik et al. |
| 2008/0114326 | A1 | 5/2008 | Roe et al. |
| 2009/0312736 | A1 | 12/2009 | Schroer, Jr. et al. |

FOREIGN PATENT DOCUMENTS

| | | |
|---|---|---|
| EP | 0409876 B1 | 7/1993 |
| EP | 0530781 B1 | 12/1998 |
| EP | 1226802 A2 | 7/2002 |
| EP | 0957865 B1 | 7/2003 |
| EP | 1642556 A1 | 4/2006 |
| EP | 1774936 A1 | 4/2007 |
| FR | 2 583 620 A1 | 12/1986 |
| JP | 05-317361 A | 12/1993 |
| JP | 10-005276 A | 1/1998 |
| JP | 2001-087311 A | 4/2001 |
| JP | 2002-291799 A | 10/2002 |
| WO | WO 95/28902 | 11/1995 |
| WO | WO 99/09159 A1 | 2/1999 |
| WO | WO 03/059603 | 7/2003 |

\* cited by examiner

DISPOSABLE ABSORBENT ARTICLE HAVING TAILORED LEG EDGES

PRIORITY

This application is a divisional of application Ser. No. 12/231,213, entitled "Disposable Absorbent Article Having Tailored Leg Edges" and filed in the U.S. Patent and Trademark Office on Aug. 29, 2008. The entirety of the prior application is hereby incorporated by reference in this application.

INTRODUCTION

Disposable absorbent articles are in widespread use in today's society. Examples of disposable absorbent articles include baby diapers, training pants, youth pants, adult incontinence garments, feminine care garments, and swimwear. There are a variety of manners in which to construct disposable absorbent articles. In one common construction, absorbent articles include a bodyside liner, a garment-side outer cover, and an absorbent core sandwiched between the liner and outer cover, which collectively define an absorbent chassis. The liner and outer cover generally extend beyond the periphery of the absorbent core, and define longitudinally extending side edges and transversely extending waist or end edges. Frequently, one or more crotch elastic members (alternatively referred to as leg elastic members) extend in the longitudinal direction and are sandwiched between the liner and outer cover in the region at least partly beyond the periphery of and to the respective sides of the absorbent core.

Due to the nature of many manufacturing techniques, the crotch elastic members do not abut the side edges of the chassis, but instead are transversely spaced inward some distance from the chassis side edges. One common example of this limitation relates to the use of "snap-back" channels. During manufacturing, the crotch elastic members are usually introduced into a continuous web assembly from a roll of elastic material, stretched, affixed to a continuous substrate, and eventually cut. To avoid the problem of the crotch elastics extending too far into the front and/or back waist regions (which can create undesirable gathering forces on the waist regions during use of the product), a portion of the longitudinal channel occupied by the elastic members is left free of adhesive near the front and/or back waist regions. When the elastic members are cut in the manufacturing process, the tensioned elastic members then "snap back" in those adhesive-free regions, with the result that the crotch elastics are "active" only in the central crotch region of the diaper, and not active in one or both of the waist regions. To accommodate the intermittent presence of crotch elastic attachment adhesive to provide such "snap back" channels, the crotch elastics must be positioned transversely inward from the chassis side edges.

Although such "snap back" channels are a useful technique to enhance the performance and appearance of absorbent articles, their use can create a problem. When the crotch elastics are spaced transversely inward from the chassis side edges, the chassis material (e.g., the liner and outer cover material) transversely outward of the crotch elastics can create "ruffles" when the garment is donned. This is because the portions of the chassis positioned transversely outward from the crotch elastics are not held snugly against the wearer, but instead tend to stick out and gather during wear. These "ruffles" can be undesirable in that the product has an unfinished, un-trim appearance when worn.

Therefore, a need exists to improve the side edge appearance of the absorbent chassis of disposable absorbent articles when worn, such as absorbent articles that include crotch elastics and "snap back" channels.

SUMMARY OF THE INVENTION

To address the problems outlined above, a new disposable absorbent article design has been invented. In one embodiment of the invention, a disposable absorbent article comprises a front waist region adjacent a front waist edge, a rear waist region adjacent a rear waist edge, and a crotch region disposed between the front waist region and the rear waist region, a central longitudinal axis extending from the front waist edge to the rear waist edge, a central transverse axis perpendicular to the longitudinal axis, and first and second crotch edges disposed on transversely opposed sides of the crotch region and extending from the front waist region to the rear waist region. The article includes a first crotch elastic member adjacent the first crotch edge and a second crotch elastic member adjacent the second crotch edge, each crotch elastic member extending generally in a longitudinal direction, each crotch elastic member having a front terminal point and a rear terminal point. At least one of the terminal points of the first crotch elastic member is positioned transversely inward from a remaining portion of the first crotch elastic member, and at least one of the terminal points of the second crotch elastic member is positioned transversely inward from a remaining portion of the second crotch elastic member.

In another embodiment of the present invention, a disposable absorbent article comprises a front waist region adjacent a front waist edge, a rear waist region adjacent a rear waist edge, and a crotch region disposed between the front waist region and the rear waist region, a central longitudinal axis extending from the front waist edge to the rear waist edge and dividing the absorbent article into first and second sides, a central transverse axis perpendicular to the longitudinal axis, and first and second crotch edges disposed on transversely opposed sides of the crotch region and extending from the front waist region to the rear waist region. The article includes a first crotch elastic member adjacent the first crotch edge and positioned entirely on the first side, and a second crotch elastic member adjacent the second crotch edge and positioned entirely on the second side, each crotch elastic member extending generally in a longitudinal direction, each crotch elastic member having a front terminal point and a rear terminal point, and each crotch elastic member defining a front end portion adjacent the front waist region, a rear end portion adjacent the rear waist region, and a central portion extending between the front and rear portions. Either the front end portions of the first and second crotch elastic members or the rear end portions of the first and second crotch elastic members converge transversely inward toward each other.

In still another embodiment of the present invention, a disposable absorbent article comprises a front waist region adjacent a front waist edge, a rear waist region adjacent a rear waist edge, and a crotch region disposed between the front waist region and the rear waist region, a central longitudinal axis extending from the front waist edge to the rear waist edge and dividing the absorbent article into first and second sides, a central transverse axis perpendicular to the longitudinal axis, and first and second crotch edges disposed on transversely opposed sides of the crotch region and extending from the front waist region to the rear waist region. The article includes a first crotch elastic member adjacent the first crotch edge and positioned entirely on the first side, and a second crotch elastic member adjacent the second crotch edge and positioned entirely on the second side, each crotch elastic member extending generally in a longitudinal direction, each crotch elastic member having a front terminal point and a rear terminal point, and each crotch elastic member defining a front end portion adjacent the front waist region, a rear end portion adjacent the rear waist region, and a central portion extending between the front and rear portions. Each crotch elastic member is sandwiched between a first layer and a second layer of the absorbent article, and portions of the first layer are unattached to the second layer to define first and second snapback channels, and both of the front and rear terminal points of the first crotch elastic member are positioned within the first snapback channel, and both of the front and rear terminal points of the second crotch elastic member are positioned within the second snapback channel. The central portion of the first crotch elastic member is positioned transversely outward of both of the front and rear terminal points of the first crotch elastic member, and the central portion of the second crotch elastic member is positioned transversely outward of both of the front and rear terminal points of the second crotch elastic member. The front end portions of the first and second crotch elastic members converge transversely inward toward each other, and the rear end portions of the first and second crotch elastic members converge transversely inward toward each other.

DEFINITIONS

Within the context of this specification, each term or phrase below will include the following meaning or meanings. Additional terms are defined elsewhere in the specification.

"Attached" refers to the joining, adhering, bonding, connecting, or the like, of two elements. Two elements will be considered to be attached together when they are attached directly to one another or indirectly to one another, such as when each is directly attached to intermediate elements.

"Bonded" refers to the joining, adhering, connecting, attaching, or the like, of two elements. Two elements will be considered to be bonded together when they are bonded directly to one another or indirectly to one another, such as when each is directly bonded to intermediate elements.

"Comprising" is inclusive or open-ended and does not exclude additional, unrecited elements or method steps.

"Connected" refers to the joining, adhering, bonding, attaching, or the like, of two elements. Two elements will be considered to be connected together when they are connected directly to one another or indirectly to one another, such as when each is directly connected to intermediate elements.

"Disposable" refers to articles which are designed to be discarded after a limited use rather than being laundered or otherwise restored for reuse.

"Disposed," "disposed on," and variations thereof are intended to mean that one element can be integral with another element, or that one element can be a separate structure bonded to or placed with or placed near another element.

"Elastic," "elasticized" and "elasticity" mean that property of a material or composite by virtue of which it tends to recover its original size and shape after removal of a force causing a deformation.

"Elastomeric" refers to a material or composite which can be elongated by at least percent of its relaxed length and which will recover, upon release of the applied force, at least 10 percent of its elongation. It is generally preferred that the elastomeric material or composite be capable of being elongated by at least 100 percent, more preferably by at least 300 percent, of its relaxed length and recover, upon release of an applied force, at least 50 percent of its elongation.

"Graphic" refers to any design, pattern, or the like that is visible on an absorbent article.

"Integral" is used to refer to various portions of a single unitary element rather than separate structures bonded to or placed with or placed near one another.

"Layer" when used in the singular can have the dual meaning of a single element or a plurality of elements.

"Longitudinal" and "transverse" have their customary meaning, as indicated by the longitudinal and transverse axes depicted in FIGS. 2 and 3. The longitudinal axis lies in the plane of the article and is generally parallel to a vertical plane that bisects a standing wearer into left and right body halves when the article is worn. The transverse axis lies in the plane of the article generally perpendicular to the longitudinal axis. The article as illustrated is longer in the longitudinal direction than in the transverse direction.

"Member" when used in the singular can have the dual meaning of a single element or a plurality of elements.

These terms may be defined with additional language in the remaining portions of the specification.

DESCRIPTION OF PARTICULAR EMBODIMENTS

Figure 1:
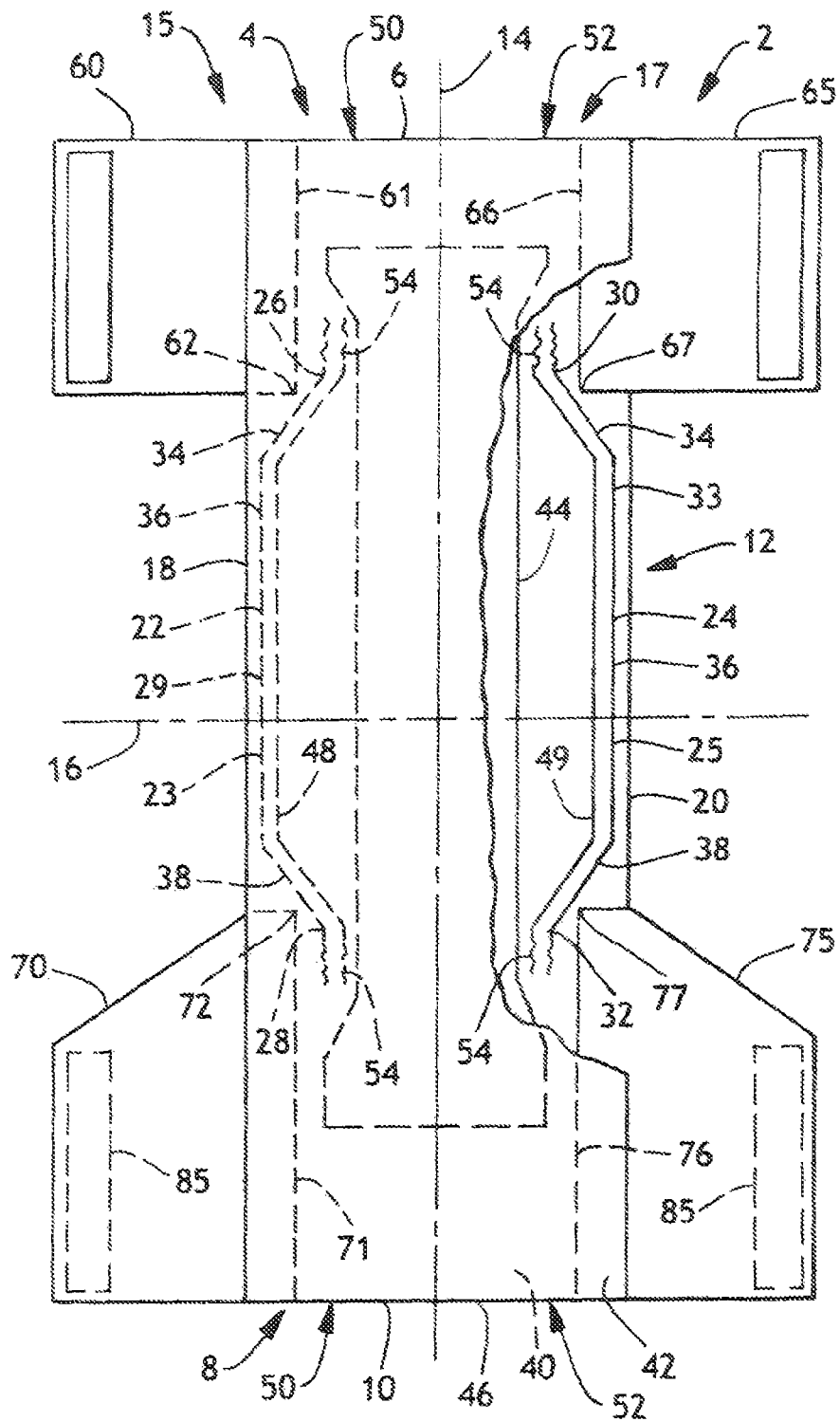
FIG. 1 illustrates a plan view of one type of disposable absorbent article incorporating the principles of the present invention, shown in an unfastened, longitudinally stretched, and laid-flat condition, and showing the surface of the article that faces away from the wearer when the article is worn, and with portions cut away to show underlying features.
Figure 2:
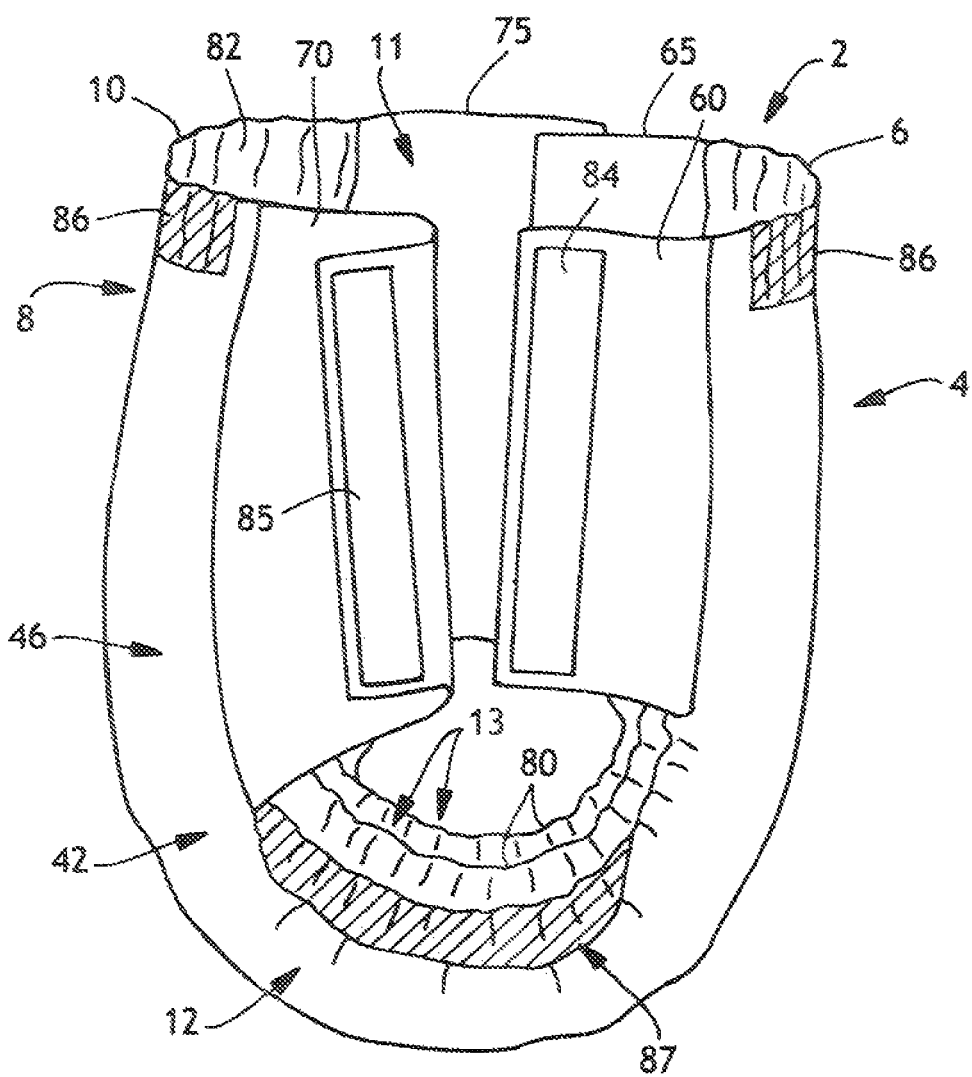
FIG. 2 illustrates a side view of one type of disposable absorbent article incorporating the principles of the present invention, where the fastening system is shown engaged on one side of the absorbent article and disengaged on the other side of the absorbent article.

Reference to FIGS. 1 and 2 shall be made in describing various embodiments of the invention. It should be noted that the embodiment depicted in FIGS. 1 and 2 is merely one representative example of the absorbent article of the invention. Although for illustrative purposes certain features of the present invention shall be described and illustrated with respect to a child's training pant, various aspects of the present invention are also suitable for use with diapers, swim pants, adult incontinence articles, and the like.

The disposable absorbent article 2 includes a front waist region 4 adjacent a front waist edge 6, a rear waist region 8 adjacent a rear waist edge 10, and a crotch region 12 disposed between the front waist region 4 and the rear waist region 8. The article 2 has a central longitudinal axis 14 extending from the front waist edge 6 to the rear waist edge 8, and a central transverse axis 16 perpendicular to the longitudinal axis 14. The longitudinal axis divides the article into a first side 15 and a second side 17. The article 2 further has a first crotch edge 18 and a second crotch edge 20 disposed on transversely opposed sides of the crotch region and which extend from the front waist region 4 to the rear waist region 8.

With the training pant 2 in the fastened position as partially illustrated in FIG. 2, the front and back waist regions 4 and 8 are joined together to define a three-dimensional pant configuration having a waist opening 11 and a pair of leg openings 13. The front waist region 4 comprises the portion of the training pant which, when worn, is positioned on the front of the wearer while the back waist region 8 comprises the portion of the training pant which, when worn, is positioned on the back of the wearer. The crotch region 12 of the training pant comprises the portion of the training pant which, when worn, is positioned between the legs of the wearer and covers the lower torso of the wearer.

The article 2 includes one or more crotch elastic members to assist in keeping the crotch region of the article snugly against the wearer during use for increased comfort and leakage protection. For example, the article can include a first crotch elastic member 22 adjacent the first crotch edge 18, and a second crotch elastic member 24 adjacent the second crotch edge 20. In particular embodiments, each crotch elastic member extends generally in a longitudinal direction. The phrase "extending generally in a longitudinal direction" means that the crotch elastic member, when viewed in its entirety, travels a longer distance in the longitudinal direction of the article than in the transverse direction of the article, and contemplates that the crotch elastic member can deviate from a strictly longitudinal path, such as, for example, by being somewhat angled relative to the longitudinal axis, or by including one or more curves over its length.

Each crotch elastic member has a front terminal point and a rear terminal point. For example, the first crotch elastic member 22 can have a front terminal point 26 and a rear terminal point 28, and the second crotch elastic member 24 can have a front terminal point 30 and a rear terminal point 32. In particular embodiments, at least one of the terminal points of each crotch elastic member is positioned transversely inward from a remaining portion of the crotch elastic member. For example, in particular embodiments, at least one of the terminal points 26 or 28 of the first crotch elastic member 22 is positioned transversely inward from a remaining portion of the first crotch elastic member 22, and at least one of the terminal points 30 or 32 of the second crotch elastic member 24 is positioned transversely inward from a remaining portion of the second crotch elastic member 24. "Transversely inward" as used herein means in a direction toward the central longitudinal axis of the article. In a preferred embodiment, both of the terminal points of each crotch elastic member are positioned transversely inward from a remaining portion of the crotch elastic member. For example, in a preferred embodiment, both the front terminal point 26 and the rear terminal point 28 of the first crotch elastic member 22 are positioned transversely inward from a remaining portion 29 of the first crotch elastic member 22, and both the front terminal point 30 and the rear terminal point 32 of the second crotch elastic member 24 are positioned transversely inward from a remaining portion 33 of the second crotch elastic member 24.

Without wishing to be bound to any theory or operative mechanism, it is believed that configuring the crotch elastics as described above can offer a product performance, fit, and/or appearance improvement. In prior art configurations, crotch elastics are spaced transversely inward from the crotch edges 18 and 20, frequently to facilitate certain processing requirements. When crotch elastics are spaced transversely inward from the crotch edges, the chassis material (e.g., the liner and outer cover material) transversely outward of the crotch elastics can create "ruffles" when the garment is donned. This is because the portions of the crotch region positioned transversely outward from the crotch elastics are not held snugly against the wearer, but instead tend to stick out and gather during wear. These "ruffles" can be undesirable in that the product has an unfinished, un-trim appearance when worn. In contrast, particular embodiments of the present invention can reduce such "ruffles" or flanges because portions of the crotch elastics are positioned relatively close to the crotch edge, with other portions of the crotch elastic positioned relatively further away from the crotch edge to accommodate various process or product restrictions. A more streamlined, tailored fit can thus be achieved.

In particular embodiments, each crotch elastic member is straight along a majority of its length to define a straight portion. For example, in particular embodiments, the first crotch elastic member 22 is straight along a majority of its length to define a straight portion 23, and the second crotch elastic member 24 is straight along a majority of its length to define a straight portion 25. "Majority" as used herein means more than fifty percent. In certain preferred embodiments, the entirety of the straight portion 23 of the first crotch elastic member 22 is positioned ten millimeters or less, and more preferably five millimeters or less, from the first crotch edge 18, and the entirety of the straight portion 25 of the second crotch elastic member 24 is positioned ten millimeters or less, and more preferably five millimeters or less, from the second crotch edge 20. Positioning the majority of the length of the first and second crotch elastic members in such relative close proximity to the crotch edges can be advantageous in reducing the aforementioned "ruffles."

In particular embodiments, the disposable absorbent article 2 includes a bodyside liner 40, garment-side outer cover 42, and an absorbent core 44 sandwiched between the liner 40 and outer cover 42. Materials suitable for use as bodyside liners, garment-side outer covers, and absorbent cores are known in the art. Examples of such materials are disclosed in U.S. Pat. No. 6,761,711 entitled "Absorbent Articles With Refastenable Side Seams" and issued Jul. 13, 2004 to Fletcher et al., the entirety of which is hereby incorporated by reference to the extent consistent herewith. The liner 40, outer cover 42, and absorbent core 44 together define a chassis 46.

In particular embodiments, the crotch elastics can be sandwiched between two layers of the chassis 46. For example, the crotch elastics 22 and 24 can be sandwiched between the bodyside liner 40 and the garment-side outer cover 42. In another example, the crotch elastics 22 and 24 can be sandwiched between two layers of a multiple-layer outer cover or a multiple-layer bodyside liner (not shown). In still another example, the crotch elastics 22 and 24 could be sandwiched between a containment flap layer and the bodyside layer of either an outer cover or a liner (not shown). In yet another example, the crotch elastics could be sandwiched between two sheets of carrier material (such as a nonwoven or film substrate), which sandwich is in turn attached to opposing crotch edges 18 and 20 (not shown). Such a sandwich of carrier material could be affixed to the bodyside surface of a bodyside liner, the garment-side surface of a garment-side outer cover, in between a bodyside liner and a garment-side outer cover, or in any other suitable manner of affixation.

In certain embodiments, such as embodiments in which each crotch elastic member is sandwiched between a bodyside liner and a garment-side outer cover, portions of the liner are unattached to the outer cover to define first and second snapback channels 50 and 52. During manufacturing, the crotch elastic members are usually introduced into a continuous web assembly from a roll of elastic material, stretched, affixed to a continuous substrate, and eventually cut. To avoid the problem of the crotch elastic members extending too far into the front and/or back waist regions (which can create undesirable gathering forces on the waist regions during use of the product), a portion of the longitudinal channel occupied by the elastic members is left free of adhesive near the front and/or back waist regions. In these adhesive-free regions, the outer cover and liner are not bonded to each other. Such adhesive-free channels can be any suitable width, such as, for example, 1 inch (25 cm). When the elastic members are cut in the manufacturing process, the tensioned elastic members then "snap back" in those adhesive-free regions (leaving a small "snapped-back," inactive portion 54 at either end of the elastic member 22/24), with the result that the crotch elastics are "active" only in the central crotch region of the diaper, and not active in the waist regions. To ensure, in particular embodiments, that the crotch elastic members are contained within the chassis, and to avoid having those "loose" portions of the chassis in which the liner and outer cover are unattached extend to the longitudinal edges of the chassis, the "snap-back" channels must generally be positioned transversely inward from the chassis side edges.

In certain embodiments in which the absorbent article includes snap-back channels 50 and 52, one or more of the terminal points of the crotch elastics can be positioned within the snapback channels. For example, in particular embodiments, at least one of the front and rear terminal points 26 and 28 of the first crotch elastic member 22 is positioned within the first snapback channel 50, and at least one of the front and rear terminal points 30 and 32 of the second crotch elastic member 24 is positioned within the second snapback channel 52. In a preferred embodiment, both the front and rear terminal points 26 and 28 of the first crotch elastic member 22 are positioned within the first snapback channel 50, and both the front and rear terminal points 30 and 32 of the second crotch elastic member 24 are positioned within the second snapback channel 52. It should be noted that in embodiments that employ a "snapped-back" elastic, the terminal points 26/28/30/32 are the endpoints of the active region of the elastic member, without regard to the position of the endpoints of the inactive portion 54 of each elastic member. That is, the terminal points denote the endpoints of the active portion of the elastic member, which may or may not be the same as the absolute endpoints of the entire elastic member.

In particular embodiments, the disposable absorbent article 2 includes one or more side panels extending transversely outward from the chassis 46. Such side panels can be separate components that are attached to the chassis, or can be integral with one or more components of the chassis, such as the liner, outer cover, both the liner and the outer cover, or a portion of either the liner or the outer cover. If separately attached, such side panels can be directly or indirectly attached to a garment-facing surface of the chassis, a body-facing surface of the chassis, or attached between two of the chassis layers, such as between a liner and an outer cover. Such side panels can be non-stretchable, stretchable but not elastomeric, or stretchable and elastomeric. Examples of side panels suitable for use in conjunction with certain embodiments of the present invention are disclosed in U.S. Pat. No. 6,761,711, earlier incorporated by reference in its entirety.

For example, in particular embodiments, first and second elastic side panels 60 and 65 extend transversely outward from and are bonded to opposing side regions of at least one of the waist regions 4 or 8. Taking the front waist region 4 as an example, each of the side panels 60 and 65 defines a transversely innermost proximal edge 61 and 66 extending generally in the longitudinal direction, and each side panel 60 and 65 defines a longitudinally innermost corner 62 and 67. In particular embodiments, the crotch elastic member terminal point closest to the first elastic side panel 60—that is, terminal point 26—is positioned transversely inward of the proximal edge 61 of the first elastic side panel 60 and longitudinally outward of the innermost corner 62 of the first elastic side panel 60. Additionally, the crotch elastic member terminal point closest to the second elastic side panel 65—that is, terminal point 30—is positioned transversely inward of the proximal edge 66 of the second elastic side panel 65 and longitudinally outward of the innermost corner 67 of the second elastic side panel 65. "Longitudinally inward" as used herein means in a direction toward the central transverse axis of the article. "Longitudinally outward" as used herein means in a direction away from the central transverse axis of the article. "Longitudinally innermost" as used herein means closest to the central transverse axis of the article. "Transversely inward" as used herein means in a direction toward the central longitudinal axis of the article. "Transversely outward" as used herein means in a direction away from the central longitudinal axis of the article. "Transversely innermost" as used herein means closest to the central longitudinal axis of the article.

In a preferred embodiment, first and second front elastic side panels 60 and 65 extend transversely outward from and are bonded to opposing side regions 15 and 17 of the front waist region 4, and first and second rear elastic side panels 70 and 75 extend transversely outward from and are bonded to opposing side regions 15 and 17 of the rear waist region 8. Each elastic side panel 60/65/70/75 defines a transversely innermost proximal edge 61/66/71/76 extending generally in the longitudinal direction, and each side panel 60/65/70/75 defines a longitudinally innermost corner 62/67/72/77. In particular embodiments, each terminal point 26/28/30/32 of each crotch elastic member is positioned transversely inward of the proximal edge of the side panel to which it is nearest and longitudinally outward of the innermost corner of the side panel to which it is nearest.

In an alternative articulation of particular embodiments of the present invention, the first crotch elastic member 22 lies adjacent the first crotch edge 18 and is positioned entirely on the first side 15, and the second crotch elastic member 24 lies adjacent the second crotch edge 20 and is positioned entirely on the second side 17. Each crotch elastic member defines a front end portion 34 adjacent the front waist region 4, a rear end portion 38 adjacent the rear waist region 8, and a central portion 36 extending between the front end and rear end portions 34 and 38. In particular embodiments, the front end portions 34 of the first and second crotch elastic members 22 and 24 converge transversely inward toward each other. In other embodiments, the rear end portions 38 of the first and second crotch elastic members 22 and 24 converge transversely inward toward each other. In a preferred embodiment, the front end portions 34 of the first and second crotch elastic members 22 converge transversely inward toward each other, and the rear end portions 38 of the first and second crotch elastic members 22 and 24 converge transversely inward toward each other. Without wishing to be bound by any theory, such a configuration can, in certain embodiments, allow all four of the terminal points 26/28/30/32 to be positioned in a snapback channel 50/52, which can allow the crotch elastic members 22/24 to snap back and provide the aforementioned fit benefits at the waist regions 4/8, and to simultaneously reside, along the central portion 36, relatively close to the crotch edges 18/20 in the crotch region 12 to provide a trim, tailored appearance during wear with reduced "ruffles" or flanges.

In particular embodiments, the absorbent article 2 can have multiple crotch elastic members on each side 15/17. For example, two, three, or four or more crotch elastics can be positioned on each side of the article. For example, as representatively illustrated in FIG. 1, a third crotch elastic member 48 and fourth crotch elastic member 49 can optionally be included to provide additional gasketing protection around the leg and crotch areas. In particular embodiments, such additional crotch elastic members can be configured in accordance with the configurations described above with respect to the first and second crotch elastic members.

The absorbent article 2 can optionally include any number of additional features, including one or more waist elastic members 82, one or more fastening components 84, one or more mating fastening components 85, and one or more graphics, such as a printed waist band graphic 86 and/or a printed leg band graphic 87. Suitable examples of such optional additional components are disclosed in U.S. Pat. No. 6,761,711, earlier incorporated by reference in its entirety. Further, the various components of the absorbent article 2 can be assembled together employing various types of suitable attachment means, such as adhesive, sonic and thermal bonds or combinations thereof.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

We claim:

1. A disposable absorbent article comprising:
a front waist region adjacent a front waist edge, a rear waist region adjacent a rear waist edge, and a crotch region disposed between the front waist region and the rear waist region, a central longitudinal axis extending from the front waist edge to the rear waist edge and dividing the absorbent article into first and second sides, a central transverse axis perpendicular to the longitudinal axis, and first and second crotch edges disposed on transversely opposed sides of the crotch region and extending from the front waist region to the rear waist region;
a first crotch elastic member adjacent the first crotch edge and positioned entirely on the first side, and a second crotch elastic member adjacent the second crotch edge and positioned entirely on the second side, each crotch elastic member extending generally in a longitudinal direction, each crotch elastic member having a front terminal point and a rear terminal point, and each crotch elastic member defining a front end portion adjacent the front waist region, a rear end portion adjacent the rear waist region, and a central portion extending between the front and rear portions,
wherein either the front end portions of the first and second crotch elastic members or the rear end portions of the first and second crotch elastic members converge transversely inward toward each other; and
further wherein each crotch elastic member is sandwiched between a bodyside liner and a garment-side outer cover, wherein portions of the liner are unattached to the outer cover to define first and second snapback channels, and wherein said at least one of the front and rear terminal points of the first crotch elastic member is positioned within the first snapback channel, and wherein said at least one of the front and rear terminal points of the second crotch elastic member is positioned within the second snapback channel.

2. The disposable absorbent article of claim 1, wherein the front end portions of the first and second crotch elastic members converge transversely inward toward each other, and the rear end portions of the first and second crotch elastic members converge transversely inward toward each other.

3. The disposable absorbent article of claim 1, where each crotch elastic member is straight along a majority of its length to define straight portion.

4. The disposable absorbent article of claim 3, wherein the entirety of the straight portion of the first crotch elastic member is positioned 5 millimeters or less from the first crotch edge, and the entirety of the straight portion of the second crotch elastic member is positioned 5 millimeters or less from the second crotch edge.

5. The disposable absorbent article of claim 1, where both of the front and rear terminal points of the first crotch elastic member are positioned within the first snapback channel, and wherein both of the front and rear terminal points of the second crotch elastic member are positioned within the second snapback channel.

6. A disposable absorbent article comprising:
a front waist region adjacent a front waist edge, a rear waist region adjacent a rear waist edge, and a crotch region disposed between the front waist region and the rear waist region, a central longitudinal axis extending from the front waist edge to the rear waist edge and dividing the absorbent article into first and second sides, a central transverse axis perpendicular to the longitudinal axis, and first and second crotch edges disposed on transversely opposed sides of the crotch region and extending from the front waist region to the rear waist region;
a first crotch elastic member adjacent the first crotch edge and positioned entirely on the first side, and a second crotch elastic member adjacent the second crotch edge and positioned entirely on the second side, each crotch elastic member extending generally in a longitudinal direction, each crotch elastic member having a front terminal point and a rear terminal point, and each crotch elastic member defining a front end portion adjacent the front waist region, a rear end portion adjacent the rear waist region, and a central portion extending between the front and rear portions,
wherein each crotch elastic member is sandwiched between a first layer and a second layer of the absorbent article, wherein portions of the first layer are unattached to the second layer to define first and second snapback channels, and wherein both of the front and rear terminal points of the first crotch elastic member are positioned within the first snapback channel, and wherein both of the front and rear terminal points of the second crotch elastic member are positioned within the second snapback channel,
wherein the central portion of the first crotch elastic member is positioned transversely outward of both of the front and rear terminal points of the first crotch elastic member, and wherein the central portion of the second crotch elastic member is positioned transversely outward of both of the front and rear terminal points of the second crotch elastic member,
and wherein the front end portions of the first and second crotch elastic members converge transversely inward toward each other, and wherein the rear end portions of the first and second crotch elastic members converge transversely inward toward each other.

7. The absorbent article of claim 6, wherein each crotch elastic member comprises at least two strands of elastic material.

8. The absorbent article of claim 6, wherein the first layer is a bodyside liner, and the second layer is a garment side outer cover.

9. The absorbent article of claim 6, wherein the first and second layers are layers of a garment-side outer cover laminate.

\* \* \* \* \*